United States Patent
Tsai et al.

(10) Patent No.: US 11,433,149 B2
(45) Date of Patent: Sep. 6, 2022

(54) MICROSPHERE AND PREPARATION METHOD THEREOF

(71) Applicant: PLATINUM OPTICS TECHNOLOGY INC., Taoyuan (TW)

(72) Inventors: Yu-Yu Tsai, Taoyuan (TW); Fu-Yu Chang, Taoyuan (TW); Chien-Liang Liu, Taoyuan (TW)

(73) Assignee: PLATINUM OPTICS TECHNOLOGY INC., Taoyuan (TW)

( * ) Notice: Subject to any disclaimer, the term of this patent is extended or adjusted under 35 U.S.C. 154(b) by 253 days.

(21) Appl. No.: 16/280,366

(22) Filed: Feb. 20, 2019

(65) Prior Publication Data

US 2020/0023088 A1    Jan. 23, 2020

(30) Foreign Application Priority Data

Mar. 5, 2018 (TW) .................... 107107235

(51) Int. Cl.
| | |
|---|---|
| *A61K 51/12* | (2006.01) |
| *G21K 5/02* | (2006.01) |
| *A61B 6/00* | (2006.01) |
| *A61N 5/10* | (2006.01) |

(52) U.S. Cl.
CPC .......... *A61K 51/1255* (2013.01); *A61B 6/481* (2013.01); *A61N 5/1007* (2013.01); *G21K 5/02* (2013.01); *A61N 2005/109* (2013.01)

(58) Field of Classification Search
None
See application file for complete search history.

(56) References Cited

FOREIGN PATENT DOCUMENTS

WO    WO-2016082045 A1 *  6/2016  ......... A61K 51/1244

* cited by examiner

*Primary Examiner* — Jennifer Lamberski
(74) *Attorney, Agent, or Firm* — Amin, Turocy & Watson, LLP (57) ABSTRACT

Provided is a microsphere including a glass sphere core. The glass sphere core includes a first nuclide, a second nuclide and a diffusion region extending inwardly from an outer surface of the glass sphere core, with the second nuclide distributed in the diffusion region. The first nuclide and the second nuclide become radioactive after being activated by neutrons to produce radiations including β-rays or γ-rays, or simultaneously β-rays and γ-rays. A preparation method of a microsphere is also provided.

12 Claims, 6 Drawing Sheets

MICROSPHERE AND PREPARATION METHOD THEREOF

BACKGROUND

1. Technical Field

The present disclosure relates to a radioactive microsphere, in particular, to a radioactive microsphere which can be used for the site-directed internal radiation therapy, and a preparation method thereof.

2. Description of Related Art

The site-directed internal radiation therapy (S.I.R.T.) is a method for treating cancer cells and solid tumors through site-directed radiation therapy. Most of the patients are treated with the S.I.R.T method for not being capable of removing by surgery, or being treated by chemotherapy with no specific effects. Every year, tens of thousands of primary cancers or metastatic cancers of liver occur in countries around the world. Traditional treatments use external radiation therapy to destroy or eliminate liver tumors, but radiation is shielded by the body. The subsequent large attenuation thus results to necessarily apply a great deal of dose of radiation. These excessive doses, however, would also cause normal liver cells adjacent to the liver tumor to be damaged simultaneously. This problem often leads to a significant drop in patient survival, which is needed to be overcome.

In order to overcome and avoid the human body exposed to the excessive radiation, a method of radioactive particles is derived from the traditional chemical embolization, and the radioactive particles are directly transmitted through the blood vessel into the tumor to reduce the risk of damage caused by the traditional radiation therapy. In fact, the traditional vascular embolization is a process of administering vascular drugs or other substance directly into the blood vessel to achieve saturation, and then the blood vessel is plugged and accelerated to form a mass. At this time, the blood flow velocity in the blood vessel is lowered or stopped. It is used to shrink the size of the tumor, or to help observe and prevent other bleeding caused by surgery. Therefore, radioactive elements can be added to the carrier structure of microspheres, metal filament or polymer resin. The radioactive elements can be directly transmitted to the site of cancer tumor through these carriers, and the microspheres can be directly administered to the arteries of the target organ.

An yttrium oxide powder of high density (5.01 g/cm$^3$) has an irregular particle shape. The high-density pure yttrium oxide powder is difficult to maintain particle suspension in the body fluid, and the sharp horn and edge of the yttrium oxide particles stimulate the peripheral tissue in the local area. Therefore, the yttrium oxide powder must undergo appropriate spheroidization. Studies have shown that glass is relatively resistant to radiation damage, extremely insoluble and non-toxic. The glass is easily and evenly spheroidized with minimal radionuclide impurities. Improvement of preparation techniques has developed glass microspheres substantially free of radioactive material leaching. The most suitable radioactive materials are $^{90}$Y, $^{188}$Re and $^{166}$Ho. All of the three substances can be used for radiation therapy of β rays. Although $^{90}$Y is often used for radionuclide therapy, $^{90}$Y has two major drawbacks in the use of radiation therapy. First, a long neutron activation time (>2 weeks) is required to achieve the therapeutic activity of yttrium because the $^{90}$Y precursor has small thermal neutrons passing through a 1.28 barn cross section. Second, the biodistribution of the $^{90}$Y microspheres cannot be directly determined in clinical trials because $^{90}$Y is a pure β-emitter and does not produce imagable γ rays. The natural rhenium consists of two isotopes, $^{185}$Re and $^{187}$Re. After neutron activation, they form the $^{186}$Re and $^{188}$Re radioisotopes that emit β, respectively. The nuclear and dosimetric properties of rhenium radioisotopes can be compared to those of $^{90}$Y, but they have imagable γ-photons. Similar to the rhenium radioisotope, $^{166}$Ho emits β particles and photons, which have a relatively short physical half-life of 26.8 h as compared to $^{90}$Y (64.1 h) and $^{186}$Re (90.6 h), resulting in a high radiation dose rate.

At the early stage, such radioactive microspheres have considerable clinical risks, including: first, adding or mixing yttrium into polymer materials, and then making the polymer material into microspheres, although the physical density property of the polymer microspheres are suitable for distribution in the human body, the radioactive $^{90}$Y leaching from the microspheres is a serious problem, resulting in non-specific radiation damage to other normal tissues; second, although polymeric ion exchange microspheres solve the problem of yttrium permeation, after the stable $^{89}$Y isotope undergoes neutron activation, the $^{90}$Y radionuclide must be added to the microspheres. This results in polymer ion exchange microspheres containing only a very low percentage of yttrium, resulting in severely insufficient radiation dose. In order to overcome these problems, a biocompatible glass material is thus used to uniformly mix a radioactive radioisotope having an α, β or γ radioactive ability, e.g., yttrium-90, into the glass material.

Two types of S.I.R.T microspheres are currently used in the market. The clinically used radioactive microspheres (TheraSphere) (MDS Nordion, Inc.) consist of glass spheres filled with $^{90}$Y. Each microsphere has a diameter of 25±10 μm, and a main effect thereof is to stay in the tumor distal arteriole. It is estimated to contain 22,000 to 73,000 microspheres per milligram. The strong chemical stability and weather resistance of the $Y_2O_3$—$Al_2O_3$—$SiO_2$ glass system prevent the $^{90}$Y radionuclide from leaching from the glass sphere. The other type is the SIR-Spheres (Sirtex Inc.) resin microsphere developed in Australia, which emphasizes that the modified PMMA resin polymer would more stably capture the $^{90}$Y radionuclide without leaching; and in combination with chemotherapy drugs, the double treatment is conducted for tumors at different sites. However, the dose of the resin-based microsphere is far less than that of the glass microsphere. A common feature of the two is that they both use the isotope $^{90}$Y, which has relatively high β energy. The yttrium-90 ($^{90}$Y) is a pure β emitter, and decays to a stable $^{90}$Zr with an average energy of 0.94 MeV and a half-life of 2.67 days (64.2 hours). In the atomic reactor, yttrium-90 undergoes neutron impact by $^{89}$Y to produce $^{90}$Y β radiation, which penetrates 2.5 mm of the living tissue and has a maximum radiation distance of 1.1 cm. A GBq (27 mCi) of $^{90}$Y in human tissue can radiate a total dose of 50 Gy/Kg.

According to the current treatment methods and dosages approved by the US FDA, such treatments can only be accepted once in a lifetime of a subject with the currently used radioactive microspheres (TheraSphere) and resin microspheres (SIR-spheres). The glass microspheres do not contain a second nuclide for postoperative tracking and imaging, and there is no application of coating and grafting to the related drugs, so that it is impossible to achieve the function of real-time imaging in vivo and tracking the distribution of microspheres of treatment subsequent radioactive decay. While resin microspheres can be combined with chemotherapeutic drugs for multiple treatments, the radiation dose of a single resin microsphere is much less than that of the glass microsphere, such that it fails to achieve the maximum ablation of tumors, and it is not conducive to subsequent treatment. Therefore, the present disclosure develops a glass microsphere having a high radiation dose, provides functions of imaging and tracking for the distribution of microspheres of treatment subsequent radioactive decay, and the glass microsphere can be combined with a chemotherapeutic drug to develop a multifunctional composite microsphere to solve the aforementioned current product drawbacks.

SUMMARY

The present disclosure provides a microsphere, comprising: a glass sphere core comprising a first nuclide, a second nuclide, and a diffusion region extending inwardly from an outer surface of the glass sphere core, wherein the second nuclide is distributed in the diffusion region, and the first nuclide and the second nuclide become radioactive after being activated by neutrons to produce radiations comprising β-rays or γ-rays, or simultaneously β-rays and γ-rays.

The present disclosure further provides a preparation method of a microsphere, comprising steps of heating glass powder comprising a first nuclide to spheroidize and form a glass sphere core; and reacting the glass sphere core with a cooling source, wherein the cooling source is a saturated liquid containing a second nuclide liquid phase component with a second nuclide diffused into the glass sphere core by being thermally activated to form a diffusion region extending inwardly from an outer surface of the glass sphere core, wherein the first nuclide and the second nuclide are radioactive after being activated by neutrons to produce radiations comprising β-rays or γ-rays, or simultaneously β-rays and γ-rays.

According to the present disclosure, the glass microsphere is provided with a second nuclide, which can provide radiation imaging and coating for drugs, combine at the same time a high radiation dose of the glass-based microsphere, and perform the function of in vivo imaging. The glass microsphere can be combined with chemotherapy drugs, so that the problems of traditional site-directed internal radiation therapy are significantly improved.

DETAILED DESCRIPTIONS

The following embodiments are provided to illustrate the disclosure of the present disclosure. One skilled in the art can easily understand the advantages and functions after reading the disclosure of the present specification.

It shall be understood that structures, proportions, dimensions, and the like of the present disclosure are for comprehension of one skilled in the art, instead of the intention of limiting the present disclosure under specific conditions, and do not have any technical significance. Without prejudice to effects and achievable objectives of this specification, modifications of any structure, changes in the proportional relationship, or adjustments to the dimensions are included within the scope of the present disclosure without departing from the scope of the disclosure. Without any substantial alteration of technical contents, changes or adjustments to the relative relationship of the present disclosure are deemed to be within the scope of the present disclosure.

The present disclosure provides a microsphere having a complex shell-like structure with a second nuclide element in a diffusion region of a glass sphere core.

Figure 1A:
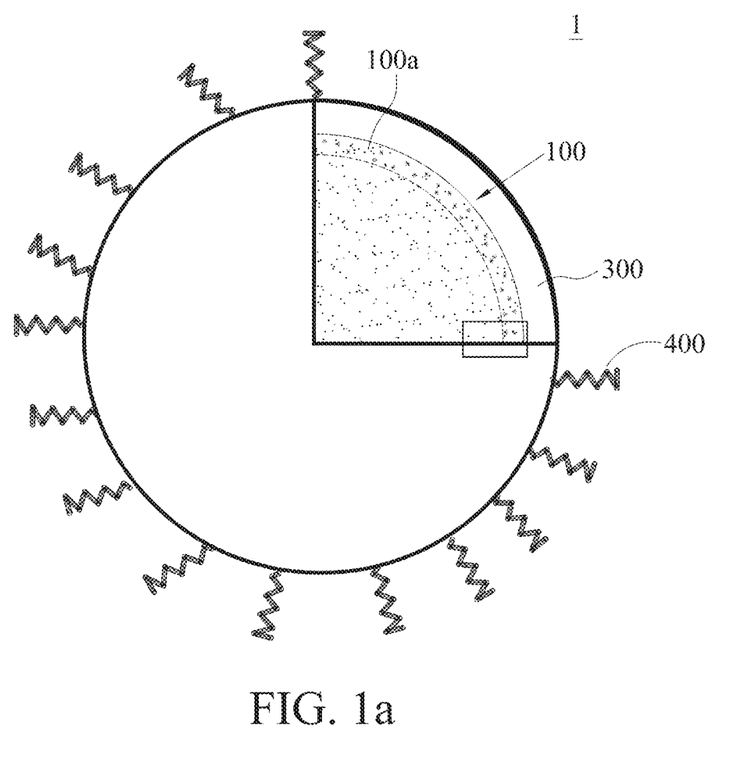
FIG. 1a is a schematic cross-sectional view of a microsphere.
Figure 1B:
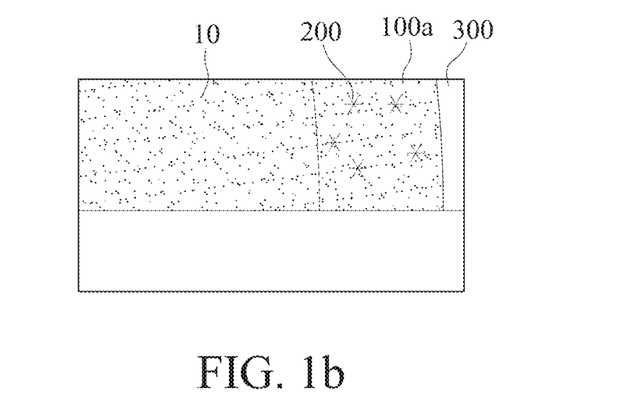
FIG. 1b is a partial enlarged view of a schematic cross section of the microsphere.

As shown in FIGS. 1a and 1b, the present disclosure provides a microsphere 1 comprising: a glass sphere core 100 comprising a first nuclide 10 and a second nuclide 200, and the glass sphere core has a diffusion region 100a. The second nuclide 200 is distributed in the diffusion region 100a, wherein the first nuclide 10 and the second nuclide 200 are radioactive after being activated by neutrons, and generate β-rays, γ-rays, or both β-rays and γ-rays. Since said second nuclide 200 is diffused into the glass sphere core 100 and distributed in the gap of the diffusion region 100a in the glass sphere core 100, it is known that the diffusion region 100a is a portion of the glass sphere core 100, rather than an applied coating.

In one embodiment, the microsphere 1 further includes a shell layer 300 covering the glass sphere core 100, and the material of the shell layer 300 is one of an organic material, an inorganic material, or a combination thereof.

The shell layer 300 can be coated with the organic material, one of the inorganic materials, or a combination thereof on the glass sphere core 100 by a spray method. In one embodiment, the organic material comprises an acid group, a hydroxyl group, an amine group or a biodegradable material; the inorganic material comprises a phosphate compound, a sulfate compound, a chloride compound, a nitrate compound or a borate compound.

In one embodiment, the organic material is selected from at least one of the group consisting of polyvinylpyrrolidone, polyvinyl alcohol, carboxymethyl cellulose, methyl cellulose, hydroxypropyl methylcellulose, hydroxypropyl cellulose, polyethylene glycol, gum arabic and a copolymer of polylactic acid and polylactic acid-glycolic acid.

In another embodiment, the shell layer 300 is further grafted with a radiotherapeutic agent or a radioactive contrast agent.

In a specific embodiment, the glass sphere core comprises a radiotherapeutic agent. Specifically, the first nuclide may be yttrium. Further, the second nuclide used in the present disclosure may be provided in the form of an isotope suspension or an oxidized acid or an alkali oxide or a dissociable salt. There is no particular limitation as long as it can achieve separation of element by a heating, dissolving or melting procedure to provide surface treatment. For example, before neutron activation, the second nuclide is selected from at least one of the group consisting of phosphorus, calcium, sodium, rhenium, scandium, lanthanum, cerium, praseodymium, neodymium, promethium, samarium, europium, gadolinium, terbium, dysprosium, holmium, erbium, thulium, ytterbium, lutetium, actinium-225, antimony-127, arsenic-74, barium-140, bismuth-210, californium-246, calcium-46, calcium-47, carbon-11, carbon-14, cesium-131, cesium-137, chromium-51, cobalt-57, cobalt-58, cobalt-60, dysprosium-165, erbium-169, fluorine-18, gallium-67, gallium-68, gold-198, holmium-166, hydrogen-3, indium-111, indium-113m, iodine-123, iodine-125, iodine-131, iridium-192, iron-59, iron-82, krypton-81m, lanthanum-140, lutetium-177, molybdenum-99, nitrogen-13, oxygen-15, palladium-103, phosphorus-32, radon-222, radium-224, rhenium-186, rhenium-188, rhodium-82, samarium-153, selenium-75, sodium-22, sodium-24, strontium-89, technetium-99m, thallium-201, xenon-127, xenon-133 and yttrium-90. Said second seed is activated by neutron activation and decays into an element represented in the brackets, phosphorus ($^{32}P\text{->}^{32}S$), calcium ($^{47}Ca\text{->}^{47}Sc$; $^{49}Ca\text{->}^{49}Sc$), sodium ($^{22}Na\text{->}^{22}Ne$), rhenium ($^{188}Re\text{->}^{188}Os$), scandium ($^{44}Sc\text{->}^{44}Ca$; $^{48}Sc\text{->}^{48}Ti$; $^{46}Sc\text{->}^{46}Ti$; $^{47}Sc\text{->}^{47}Ti$), lanthanum ($^{140}La\text{->}^{140}Ce$; $^{142}La\text{->}^{142}Ce$), cerium, praseodymium, neodymium, promethium, samarium, europium, gadolinium, terbium, dysprosium, holmium, erbium, thulium, ytterbium, lutetium, actinium-225 ($^{225}Ac\text{->}^{221}Fr,^{211}Bi,^{14}C$), antimony-127 ($^{127}Sb\text{->}^{127}Te$), arsenic-74 ($^{74}As\text{->}^{74}Ge$), barium-140 ($^{140}Ba\text{->}^{140}La$), bismuth-210 ($^{210}Bi\text{->}^{210}Po$), californium-246 ($^{246}Cf\text{->}^{246}Cm$), calcium-46 ($^{46}Ca\text{->}^{46}Sc$), calcium-47 ($^{47}Ca\text{->}^{47}Sc$), carbon-11 ($^{11}C\text{->}^{11}B$), carbon-14 ($^{14}C\text{->}^{14}N$), cesium-131 ($^{131}Cs\text{->}^{131}Xe;^{131}Cs\text{->}^{131}Ba$), cesium-137 ($^{137}Cs\text{->}^{137}Ba$), chromium-51 ($^{51}Cr\text{->}^{51}V$), cobalt-57 ($^{57}Co\text{->}^{57}Fe$), cobalt-58 ($^{58}Co\text{->}^{58}Fe$), cobalt-60 ($^{60}Co\text{->}60Ni$), dysprosium-165 ($^{165}Dy\text{->}^{165}Ho$), erbium-169 ($^{169}Er\text{->}^{169}Tm$), fluorine-18 ($^{18}F\text{->}^{18}O$), gallium-67 ($^{67}Ga\text{->}^{67}Zn$), gallium-68 ($^{68}Ga\text{->}^{68}Zn$), gold-198 ($^{198}Au\text{->}^{198}Hg$), holmium-166 ($^{166}Ho\text{->}^{166}Er$), hydrogen-3 ($^{3}H\text{->}^{3}He$), indium-111 ($^{111}In\text{->}^{111}Cd$), indium-113m ($^{113m}In\text{->}^{113}Sn$), iodine-123 ($^{123}I\text{->}^{123}Te$), iodine-125 ($^{125}I\text{->}^{125}Te$), iodine-131 ($^{131}I\text{->}^{131}Xe$), iridium-192 ($^{192}Ir\text{->}^{192}Os,^{192}Po$), iron-59 ($^{59}Fe\text{->}^{59}Co$), krypton-81m ($^{81m}Kr\text{->}^{81}Br$), lanthanum-140 ($^{140}La\text{->}^{140}Ce$), lutetium-177 ($^{177}Lu\text{->}^{177}Hf$), molybdenum-99 ($^{99}Mo\text{->}^{99}Tc,99Ru$), nitrogen-13 ($^{13}N\text{->}^{13}C$), oxygen-15 ($^{15}O\text{->}^{15}N$), palladium-103 ($^{103}Pd\text{->}^{103}Rh$), Phosphorus-32 ($^{32}P\text{->}^{32}S$), radon-222 ($^{222}Rn\text{->}^{218}Po$), radium-224 ($^{224}Ra\text{->}^{220}Rn,^{210}Pb,^{14}C$), rhenium-186 ($^{186}Re\text{->}^{186}Os,^{186}W$), rhenium-188 ($^{188}Re\text{->}^{188}Os$), samarium-153 ($^{153}Sm\text{->}^{153}Eu$), selenium-75 ($^{75}Se\text{->}^{75}As$), sodium-22 ($^{22}Na\text{->}^{22}Ne$), sodium-24 ($^{24}Na\text{->}^{24}Mg$), strontium-89 ($^{89}Sr\text{->}^{89}Y$), technetium-99m ($^{99}Tc\text{->}^{99}Ru$), thallium-201 ($^{201}Ti\text{->}^{201}Hg$), xenon-127 ($^{127}Xe\text{->}^{127}Cs$), xenon-133 ($^{133}Xe\text{->}^{133}Cs$) and yttrium-90 ($^{99}Y\text{->}^{99}Sr$).

In one embodiment, the second nuclide element used in the present disclosure is not limited to an isotope suspension or an oxidized acid or an alkali oxide or a dissociable salt. As long as it can be used for diagnosis, treatment, and research of diseases by intravenous, oral, or inhalation of a small amount of radioisotope preparation, according to its in vivo distribution or in vitro quantification, it can be used to provide elements of the second nuclide. These radionuclides have specific affinities for specific organs, bones or tissues. They emit γ-rays and can be passed through special photographic equipment in vitro. For example, the γ camera or positron tomography scanner is used to detect its distribution and metabolism in vivo. The integration of photographic equipment with computers can display images, and can be calculated and analyzed for more information. Since most diseases have physiological, biochemical, and metabolic changes in the early stages of the disease, and then structural changes occur, most of X-ray examinations, computerized tomography, etc. are used to detect physical structures. Nuclear imaging can detect abnormalities before the onset of the disease and the presence of symptoms in other examination methods because it can show the physiological changes of the organ tissues. This ability to diagnose early often allows the disease to be treated before the disease rapidly progresses.

Figure 2:
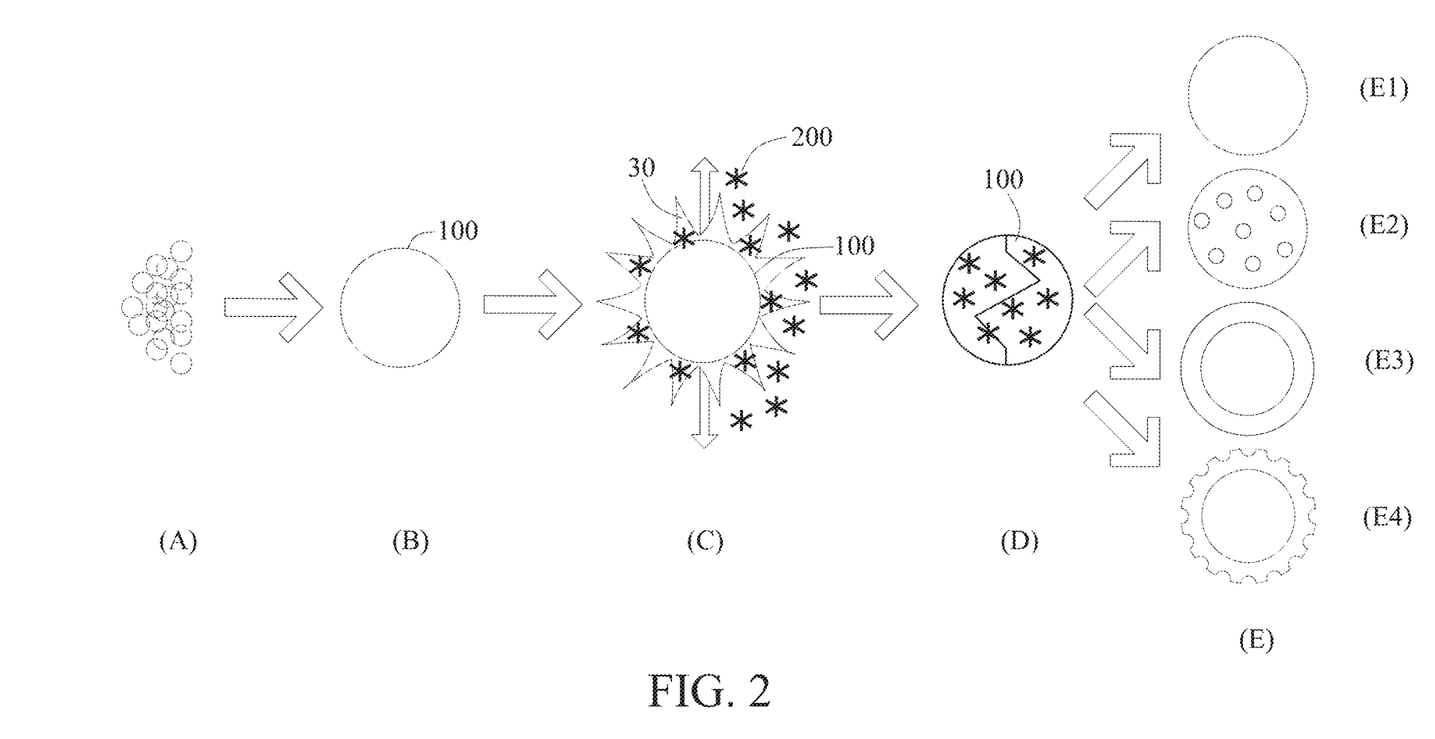
FIG. 2 is a flow chart showing the preparation method of the radioactive microsphere.

The present disclosure also provides a method of making a microsphere using a heat activation technique. As shown in FIG. 2(A), the preparation method of the microspheres comprises grinding the glass powder containing the first nuclide. Next, as shown in FIG. 2(B), the glass powder containing the first nuclide is heated and spheroidized to form a glass sphere core 100. The glass sphere core 100 is reacted with a cooling source 30 as shown in FIGS. 2(C) and (D). The cooling source 30 is a saturated liquid containing a liquid phase component of the second nuclide 200, and the second nuclide 200 of the liquid phase component of the second nuclide 200 is thermally activated and is diffused into the glass sphere core 100 to form a diffusion region 100a extending inwardly of an outer surface of the glass sphere core 100, wherein the first nuclear species and the second nuclide 200 are radioactive after being activated by neutrons, and generate β-rays, γ-rays or both β-rays and γ-rays of the rays.

The cooling source is a saturated liquid rich in the liquid phase component of the second nuclide, and the element of the second nuclide in the second seed liquid phase component is diffused into the glass spheroid core by the method of dropping and ion diffusion. The second nuclide plasma is diffused into the surface of a glass sphere core by a heat activation technique to produce a biomedical implant containing a second nuclide in the diffusion zone of the glass sphere core.

On the other hand, as shown in FIG. 2 (E1) to (E4) and Table 3, under different process conditions of different flight distances and different flames, the glass microspheres are finally separated from the flame center distance. The morphology forms a solid sphere (E1) or a surface microporous sphere (E2) or a hollow sphere (E3) or a surface roughening sphere (E4), wherein the composition of the flame depends on the mixing ratio of the combustion gas and the oxygen. A mixing ratio of oxygen and acetylene in the oxidizing flame ($Nm^3/hr$) is greater than 1.2, and the oxygen excess flame is oxidizing; a mixing ratio of oxygen to acetylene in neutral flame is 1.1 to 1.2, and oxygen and acetylene are fully burned; no oxygen and acetylene are excessive, and an inner flame has a certain reducing property; also, the $CO_2$ and CO produced by combustion have protecting effects; a mixing ratio of oxygen to acetylene in the carbonized flame is less than 1.1, which makes the acetylene excess; it has strong reducibility, and has free carbon and excessive hydrogen in the flame.

The surface treatment method of the glass material of the biomedical glass microsphere implant according to the present disclosure mainly causes the second nuclide element to diffuse into the diffusion region of the glass sphere core by the principle of heat diffusion. For example, the phosphorus ion is thermally chemically diffused. Calcium ions enter the surface of the glass material by means of temperature diffusion, but are not limited thereto.

In one embodiment, in the second nuclide used in the present disclosure, the source of the phosphorus ions is to first separate the elements by heating, dissolving or melting phosphorus-containing oxidizing acid or alkali oxide or dissociable salt. A treatment solution containing ions is thus formed. When the surface of the glass material is in contact with the treatment solution under the condition of heat activation, the surface of the glass material is activated as the increased temperature rises, and a large amount of ions in the treatment solution compete for adsorption on the activated surface. At this time, by catalysis of the chemical reaction on the surface, some of the atoms constituting the glass material react and exchange with the ions in the treatment solution, and the ions gradually diffuse into the glass material structure. In the above ion diffusion replacement process, ions with a small ionic radius are affected by the heating temperature, take the lead and gradually diffuse from the surface of the glass into the diffusion region of the glass sphere core. Specifically, the yttrium-containing glass powders are pre-milled and uniformly mixed, and then is heated and sprayed by high-speed gas flame. The glass powder is heated by the high-temperature combustion flame to cause the surface to melt, and the high-temperature molten droplets are formed under influence of the surface tension. During the rotary flight, the high-temperature molten droplets gradually form spherical shape under influence of the air temperature gradient, the gravity and the droplet rotation. As the distance from the flame center increases, the high-temperature molten droplets contact the second nuclide contained in the cooling source in the end, and because of suddenly reduced temperature gradient, spherical glass microspheres are formed, while the glass ion (yttrium) in the surface of the glass sphere core and the phosphorus ion with smaller ionic radius interact with the second nuclide in the solution. The ions having the second nuclide component in the solution diffuse into the glass microsphere material to carry out the temperature diffusion of the calcium ions. At this stage, the ion-containing cooling source, obtained by separating the elements by heating, dissolving or melting the calcium-containing compound, with drastically change of temperature, seal all the ions in the diffusion region of the glass sphere core, allowing them to adjust the surface stress to diffuse into the glass material as the temperature changes. During the process, the calcium ions gradually diffuse into the glass material structure, and as the temperature rises, the ions with smaller ionic radius also diffuse into the glass material beyond the activation energy.

Since the present disclosure utilizes the method of heating and chemically activating the surface to diffuse the second nuclide element into the diffusion region of the glass sphere core in the microsphere, the cold quenching and cooling can be rapidly carried out under controlling the parameters of ion molar concentration and temperature. So that the second nuclide, e.g., phosphorus and calcium ions, diffusing into the glass sphere core is rapidly sealed into the diffusion zone of the heated and activated glass sphere core, thereby controlling the proportion and diffusion depth of the ions in the formed composite layer. In addition, by further heating the glass material that has been subjected to cold quenching and cooling, the sealed ions can continue to diffuse in the composite layer structure and enter an appropriate cell gap to achieve structural stability.

In addition, in the surface treatment method of the glass material of the microsphere of the present disclosure, the second seed such as phosphorus and calcium can directly diffuse into the diffusion region of the glass sphere core. It can also apply heat treatment to the glass material first, allowing oxygen to enter the surface of the glass material to thicken the diffusion region before carrying out the foregoing surface treatment.

The phosphorus-containing oxidizing acid or the oxidizing base or the dissociable salt used in the present disclosure is not particularly limited as long as it is capable of achieving separation of elements by heating, dissolving or melting to provide needed elements for the surface treatment. It shall be, however, suitable for medical use, e.g., medical inorganic acid. Further, the inorganic salt-containing compound used in the present disclosure is not particularly limited as long as it is capable of achieving separation of elements by heating, dissolving or melting to provide the surface treatment. However, a pharmaceutical grade inorganic salt is better. Preferably, for example, pharmaceutical grade calcium carbonate, calcium acetate, calcium lactate, calcium citrate or the like is applicable.

The heat activation technique employed in the present disclosure preferably has a temperature in the range of from about 125° C. to about 250° C., preferably, from 165° C. to 175° C. When the heating temperature is lower than 125° C., the reaction solution is not easily observed in the interface; when the heating temperature exceeds 400° C., an unfavorable result of the dimensional change of the glass material may occur.

The present disclosure illustrates the details by way of examples of the embodiments. However, the interpretation of the present disclosure should not be limited to the following examples. The process conditions of the examples are shown in Table 3.

Figure 3:
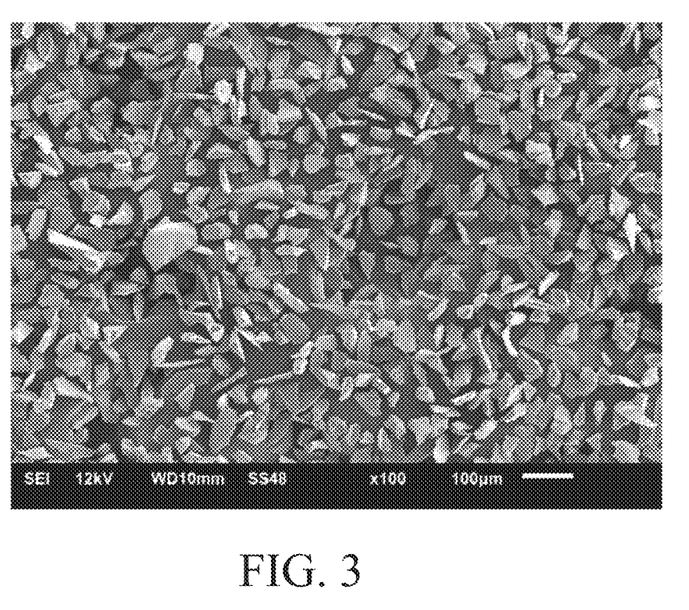
FIG. 3 is a scanning electron microscope image amplified 100 times of the glass powder of an embodiment.
Figure 4:
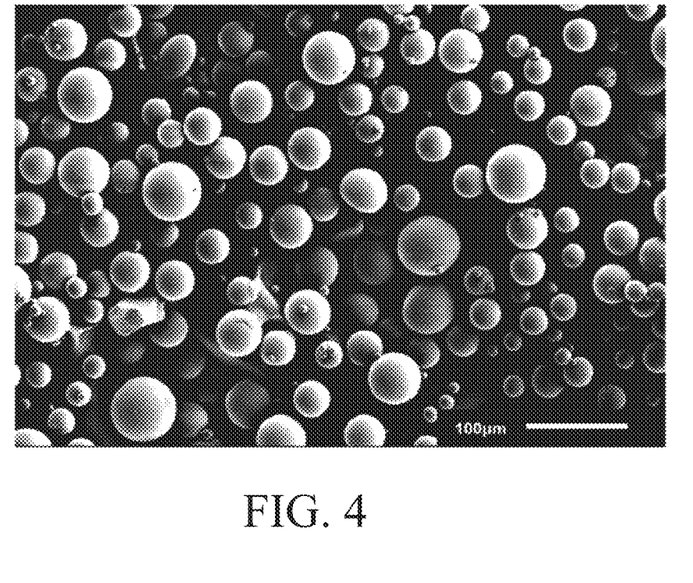
FIG. 4 is a scanning electron microscope image amplified 200 times of the solid sphere of FIG. 2 (E1)

Example I 10 mg of yttrium-containing glass powders as shown in the electron microscope of FIG. 3 was taken; the glass powders were pre-milled and uniformly mixed as shown in FIG. 2 (A), and the heating spheroidizing molding process was then carried out; a high-speed gas flame mixed with acetylene and oxygen (gas ratio 1.1 to 1.2) was heated and sprayed, and the mixed glass powder was heated by the flame. As the high-speed combustion gas was sprayed away from the flame core, the glass powders were heated by the high-temperature combustion flame to cause the surface to melt, and the high-temperature molten droplets were formed under influence of the surface tension. During the rotary flight, the high-temperature molten droplets gradually formed spherical shape under influence of the air temperature gradient, the gravity and the droplet rotation as shown in FIG. 2(B). As the distance from the flame center increases, the high-temperature molten droplets in the end contacted the second nuclide in the cooling source, i.e., a NaCl saturated liquid rich in the second nuclide liquid phase component, as shown in FIG. 2(C). Due to the suddenly reduced temperature gradient, spherical glass microspheres were formed, while the glass ion (yttrium) in the surface of the glass sphere core interacted with the second nuclide (Na ions/Cl ions) in the solution; when the ion (Na ions/Cl ions) in the solution diffused into the glass microsphere material, the temperature diffusion (Na ions/Cl ions) was carried out as shown in FIG. 2(D). Finally, the second nuclide (Na ions/Cl ions) was diffused into the glass sphere core of the microsphere by a heat activation technique, thereby producing a biomedical implant having a composite layer of a diffusion region extending inwardly from an outer surface of the glass sphere core and containing elements such as the second nuclide to form a solid glass microsphere, as shown in FIG. 2 (E1). After neutron activation element analysis, it was observed that a Na signal appeared after neutron activation, as shown in the neutron irradiation activation element analysis of Table 1. At last, a solid sphere as shown in the electron microscope of FIG. 4 was obtained.

Example II

Figure 5:
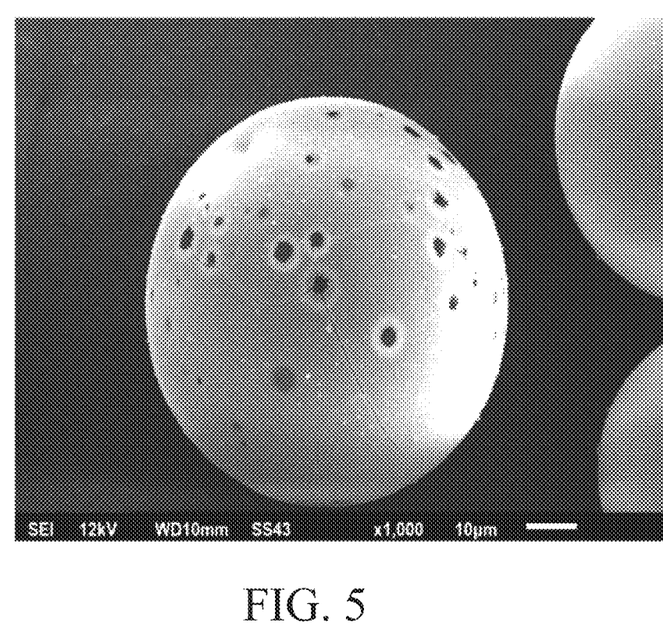
FIG. 5 is a scanning electron microscope image amplified 1000 times of the surface microporous sphere of FIG. 2 (E2)

The preparation method and conditions of Example II were as described in Example I, except that the saturated liquid rich in the second nuclide liquid phase component is $CuSO_4$ saturated liquid. Finally, the second nuclide (Cu ions/S ions) was diffused into the glass sphere core of the microsphere by a heat activation technique, thereby producing a biomedical implant of a composite layer of a diffusion region extending inwardly from an outer surface of the glass sphere core and containing elements such as the second nuclide to form a surface microporous glass microsphere, as shown in FIG. 2(E2). After neutron activation element analysis, it was observed that a Cu signal appeared after neutron activation, as shown in the neutron irradiation activation element analysis of Table 1. At last, a surface microporous glass microsphere as shown in the electron microscope of FIG. 5 was obtained.

Example III

Figure 6:
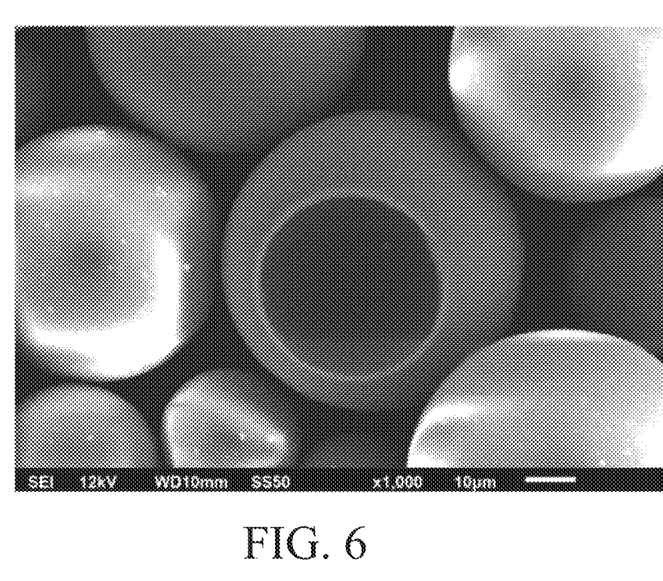
FIG. 6 is a scanning electron microscope image amplified 1000 times of the hollow sphere of FIG. 2 (E3)
Figure 7:
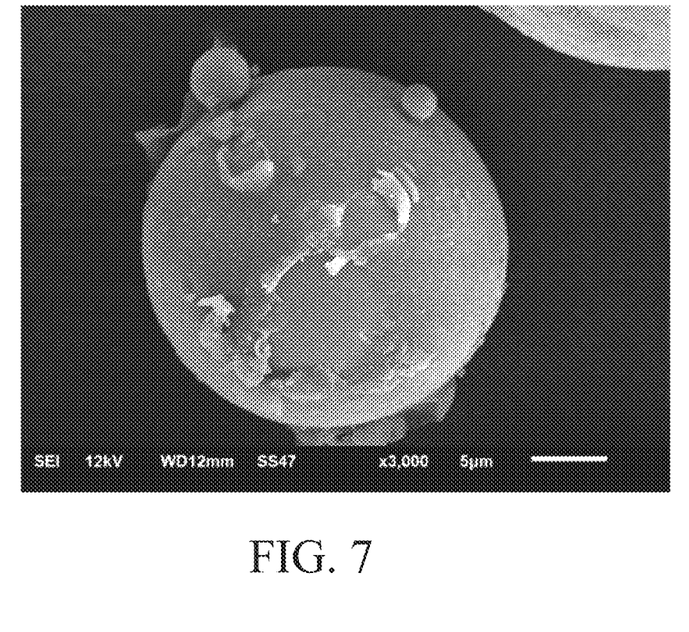
FIG. 7 is a scanning electron microscope image amplified 200 times of the surface roughening sphere of FIG. 2 (E4)

The preparation method and conditions of the embodiment (3) were as described in Example I, except that the saturated liquid rich in the second nuclide liquid phase component is $CaCl_2$ saturated liquid. Finally, the second nuclide (Ca ions/Cl ions) was diffused into the glass sphere core of the microsphere by a heat activation technique, thereby producing a biomedical implant of a composite layer of a diffusion region extending inwardly from an outer surface of the glass sphere core and containing elements such as the second nuclide to form a hollow glass microsphere, as shown in FIG. 2 (E3). After neutron activation element analysis, it was observed that a Ca signal appeared after neutron activation, as shown in the neutron irradiation activation element analysis of Table 1. At last, a hollow sphere as shown in the electron microscope of FIG. 6 was obtained.

Example IV

The preparation method and conditions of Example IV were as described in Example I, except that the saturated liquid rich in the second nuclide liquid phase component is $H_3PO_4$ saturated liquid. Finally, the second nuclide (P ions) was diffused into the glass sphere core of the radioactive microsphere by a heat activation technique, thereby producing a biomedical implant of a composite layer of a diffusion region extending inwardly from an outer surface of the glass sphere core and containing elements such as the second nuclide to form a solid glass microsphere, as shown in FIG. 2 (E1). After neutron activation element analysis, it was observed that a P signal appeared after neutron activation, as shown in the neutron irradiation activation element analysis of Table 1. At last, a solid sphere as shown in the electron microscope of FIG. 4 was obtained.

Example V

The preparation method and conditions of Example V were as described in Example I, except that the saturated liquid rich in the second nuclide liquid phase component is $TeCl_4$ saturated liquid. Finally, the second nuclide (Te ions/Cl ions) was diffused into the glass sphere core of the microsphere by a heat activation technique, thereby producing a biomedical implant of a composite layer of a diffusion region extending inwardly from an outer surface of the glass sphere core and containing elements such as the second nuclide to form a surface microporous glass microsphere, as shown in FIG. 2 (E2). After neutron activation element analysis, it was observed that a (Te ions/Cl ions) signal appeared after neutron activation, as shown in the neutron irradiation activation element analysis of Table 1. At last, a surface microporous glass microsphere as shown in the electron microscope of FIG. 5 was obtained.

Example VI

The preparation method and conditions of Example VI were as described in Example I, except that the saturated liquid rich in the second nuclide liquid phase component is $ReCl_3$ saturated liquid. Finally, the second nuclide (Re ions/Cl ions) was diffused into the glass sphere core of the microsphere by a heat activation technique, thereby producing a biomedical implant of a composite layer of a diffusion region extending inwardly from an outer surface of the glass sphere core and containing elements such as the second nuclide to form a hollow glass microsphere, as shown in FIG. 2 (E3). After neutron activation element analysis, it was observed that a (Re ions/Cl ions) signal appeared after neutron activation, as shown in the neutron irradiation activation element analysis of Table 1. At last, a hollow sphere as shown in the electron microscope of FIG. 6 was obtained.

Figure 8:
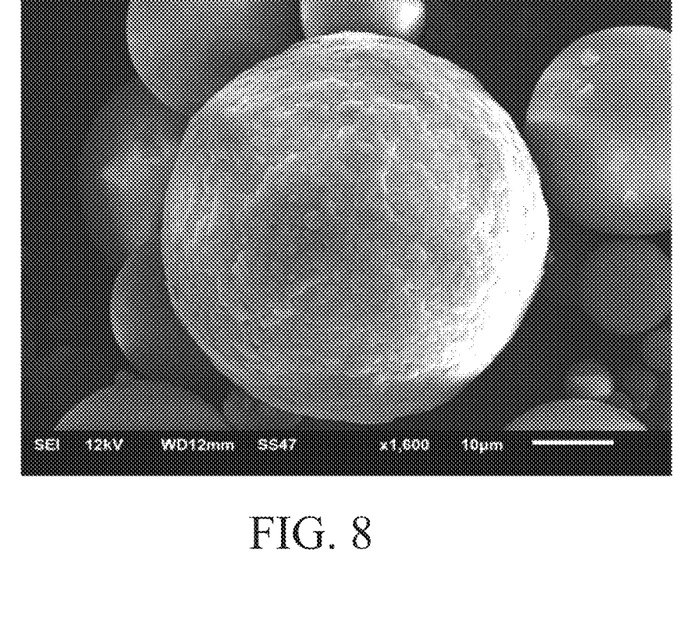
FIG. 8 is a scanning electron microscope image amplified 1600 times of a CMC coated shell.
Figure 9:
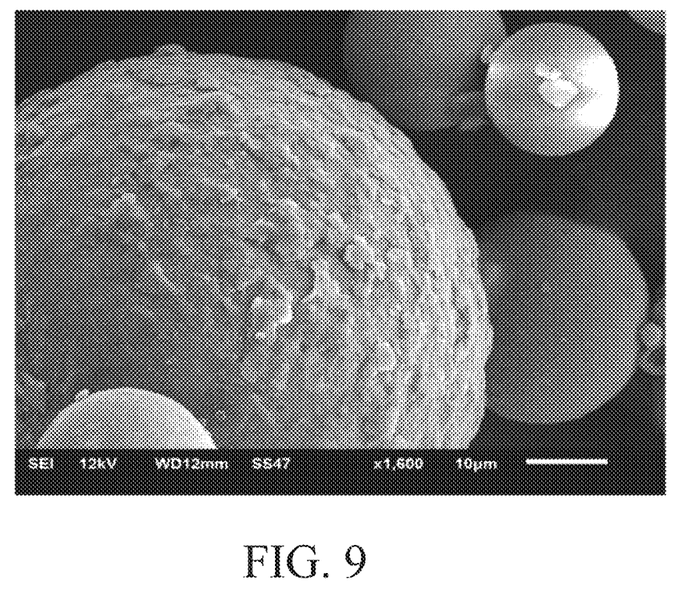
FIG. 9 is a scanning electron microscope image amplified 1600 times of a PVA coated shell.
Figure 10:
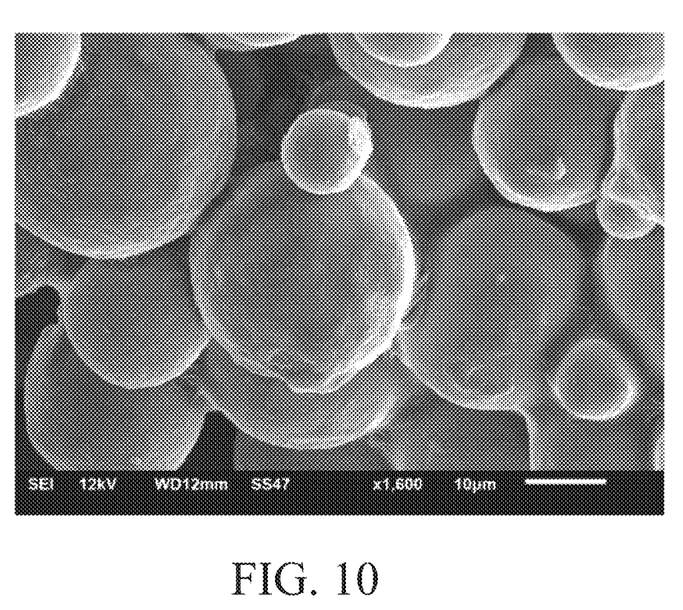
FIG. 10 is a scanning electron microscope image amplified 1600 times of a PVP coated shell.

Example VII 10 mg of yttrium-containing glass spheres of Example I were taken for spray granulation coating test with different types of organic materials and inorganic materials as shown in Table 2. The relative weight percentage of 0.1 to 10% was set to be uniformly wet-mixed with the sphere (1:1), and then coated by a spray dryer. A flow rate was set at 357 L/h and an outlet temperature was from 180 to 245° C. All of the resulting powder can be coated to form a ball, as shown in FIGS. 8 to 10.

TABLE 1

Neutron irradiation activation element analysis

| Compound | Test item weight | Radio-isotope | γ-ray energy spectrum main peak energy (keV) | AUC (cnts) | Bq | Specific activity (uCi/mg) |
|---|---|---|---|---|---|---|
| 1 Y, Na | 10 mg | Y-90 m | 202 | 264 | 43.1 | 0.00012 |
| 2 Y, Cu | 10 mg | Y-90 m | 202 | 410 | 66.9 | 0.00018 |
| 3 Y, Ca | 10 mg | Y-90 m | 202 | 393 | 64.1 | 0.00017 |
| 4 Y, P | 10 mg | Y-90 m | 202 | 290 | 47.3 | 0.00013 |
| 5 Y, Te | 10 mg | I-131 | 364.5 | 20 | 3.9 | 0.00001 |
| 6 Y, Te | 10 mg | Y-90 m | 202 | 288 | 47.0 | 0.00013 |
| 7 Y, Re | 10 mg | Re-188 | 155.1 | 1524 | 1612.7 | 0.00435 |
| 8 Y, Re | 10 mg | Y-90 m | 202 | 236 | 38.5 | 0.00010 |

TABLE 2

Organic materials and inorganic materials coating microspheres of Example VII

| Test coating material | Weight percentage | Flow rate (L/h) | Outlet temperature (° C.) | Formability |
|---|---|---|---|---|
| Polyvinylpyrrolidone (PVP) | 0.1-10 | 357 | 180-245 | Yes |
| polyvinyl alcohol (PVA) | 0.1-10 | 357 | 180-245 | Yes |
| Carboxymethyl Cellulose (CMC) | 0.1-10 | 357 | 180-245 | Yes |
| PEG 6000 | 0.1-10 | 357 | 180-245 | Yes |
| Methylcellulose (MC) | 0.1-10 | 357 | 180-245 | Yes |
| Hydroxypropyl methylcellulose (HPMC) | 0.1-10 | 357 | 180-245 | Yes |
| Hydroxypropyl cellulose (HPC) | 0.1-10 | 357 | 180-245 | Yes |
| Gum arabic | 0.1-10 | 357 | 180-245 | Yes |
| Methylcellulose (MC) | 0.1-10 | 357 | 180-245 | Yes |
| Copolymer of polylactic acid and polylactic acid-glycolic acid (PLLA/PLGA) | 0.1-10 | 357 | 180-245 | Yes |
| $Ca_3(PO_4)_s$ | 0.1-10 | 357 | 180-245 | Yes |

TABLE 3

Reaction parameters and conditions of Examples I to VI

| Example | First nuclide (composed of glass powders) | Second nuclide (cooling source) | Flame composition (Mixing ratio of oxygen and acetylene) ($Nm^3$/hr) | Flight distance from flame center to cooling source (inch) | Microsphere type FIG |
|---|---|---|---|---|---|
| I | yttrium | NaCl saturated liquid | 1.0~1.5 | 40 | Solid glass microsphere FIG. 2 (E1) |
| II | yttrium | $CuSO_4$ saturated liquid | 1.0~1.5 | 10 | Surface microporous glass microsphere FIG. 2 (E2) |
| III | yttrium | $CaCl_2$ saturated liquid | 1.0~1.5 | 150 | Hollow glass microsphere FIG. 2 (E3) |
| IV | yttrium | $H_3PO_4$ saturated liquid | 1.0~1.5 | 80 | Solid glass microsphere FIG. 2 (E1) |
| V | yttrium | $TeCl_4$ Saturated liquid | 1.0~1.5 | 30 | Surface microporous glass microsphere FIG. 2 (E2) |
| VI | yttrium | $ReCl_3$ saturated liquid | 1.0~1.5 | 100 | Hollow glass microsphere FIG. 2 (E3) |

What is claimed is:

1. A microsphere, comprising:
a glass sphere core comprising a first nuclide, a second nuclide, and a diffusion region extending inwardly from an outer surface of the glass sphere core, wherein the size of the diffusion region is less than the size of the glass sphere core,
wherein the first nuclide is distributed throughout the glass sphere core, the second nuclide is only distributed in the diffusion region and not present out of the diffusion region, and the first nuclide and the second nuclide both are capable of being radioactive to produce radiations comprising γ-rays or β-rays, or simultaneously γ-rays and β-rays.

2. The microsphere of claim 1, further comprising a shell layer coating the glass sphere core.

3. The microsphere of claim 2, wherein a material of the shell layer comprises one of an organic material, an inorganic material, or a combination thereof.

4. The microsphere of claim 1, wherein the first nuclide comprises one of yttrium, aluminum, silicon, or a combination thereof.

5. The microsphere of claim 1, wherein the second nuclide is at least one selected from the group consisting of: phosphorus, calcium, sodium, rhenium, scandium, lanthanum, cerium, praseodymium, neodymium, promethium, samarium, europium, gadolinium, terbium, dysprosium, erbium, thulium, ytterbium, lutetium, actinium, antimony, arsenic, barium, bismuth, californium, carbon, cesium, chromium, cobalt, fluorine, gallium, gold, holmium, hydrogen, indium, iodine, iridium, iron, krypton, molybdenum, nitrogen, oxygen, palladium, radon, radium, rhodium, selenium, strontium, technetium, thallium, xenon and yttrium.

6. The microsphere of claim 3, wherein the material is an organic material, and the organic material comprises an acid group, a hydroxyl group, an amine group or a biodegradable material.

7. The microsphere of claim 6, wherein the organic material is at least one selected from the group consisting of polyvinylpyrrolidone, polyvinyl alcohol, carboxymethyl cellulose, methyl cellulose, hydroxypropyl methylcellulose, hydroxypropyl cellulose, polyethylene glycol, gum arabic and a copolymer of polylactic acid and polylactic acid-glycolic acid.

8. The microsphere of claim 3, wherein the material is an inorganic material, and the inorganic material comprises a phosphate compound, a sulfate compound, a chlorine salt compound, a nitrate compound or a borate compound.

9. The microsphere of claim 3, wherein the shell layer is further grafted with a radioactive therapeutic agent or a radioactive contrast agent.

10. A method for preparing a microsphere, comprising:
heating glass powder comprising a first nuclide to spheroidize and form a glass sphere core; and
reacting the glass sphere core with a cooling source, wherein the cooling source is a saturated liquid containing a second nuclide liquid phase component with a second nuclide diffused into the glass sphere core by being thermally activated to form a diffusion region extending inwardly from an outer surface of the glass sphere core,
wherein the first nuclide and the second nuclide are capable of being radioactive to produce radiations comprising β-rays or γ-rays, or simultaneously β-rays and γ-rays.

11. The method of claim 10, further comprising forming a shell layer coating the glass sphere core by a spray process.

12. The method of claim 11, wherein the shell layer is grafted with a radioactive therapeutic agent or a radioactive contrast agent.

* * * * *